United States Patent
Xiong et al.

(10) Patent No.: US 7,539,528 B2
(45) Date of Patent: May 26, 2009

(54) USING MAGNETIC RESONANCE IMAGING TO DIRECTLY MAP NEURONAL ACTIVITY

(76) Inventors: Jinhu Xiong, 33 Colwyn Ct., Iowa City, IA (US) 52245; Jia-Hong Gao, 5712 Sage Hollow, San Antonio, TX (US) 78249; Peter T. Fox, 11831 Elmscourt, San Antonio, TX (US) 78230

( * ) Notice: Subject to any disclaimer, the term of this patent is extended or adjusted under 35 U.S.C. 154(b) by 307 days.

(21) Appl. No.: 10/666,162

(22) Filed: Sep. 18, 2003

(65) Prior Publication Data
US 2004/0096395 A1      May 20, 2004

Related U.S. Application Data

(60) Provisional application No. 60/412,171, filed on Sep. 20, 2002.

(51) Int. Cl.
*A61B 5/055* (2006.01)
(52) U.S. Cl. .................. 600/411; 600/410
(58) Field of Classification Search ........ 600/410, 600/418, 544, 545, 407, 420, 424, 411, 427, 600/428, 429, 409
See application file for complete search history.

(56) References Cited

U.S. PATENT DOCUMENTS

| | | | | |
|---|---|---|---|---|
| 4,940,453 A * | 7/1990 | Cadwell | | 600/13 |
| 5,047,005 A * | 9/1991 | Cadwell | | 600/13 |
| 5,603,322 A * | 2/1997 | Jesmanowicz et al. | | 600/410 |
| 5,725,471 A * | 3/1998 | Davey et al. | | 600/13 |
| 5,885,215 A * | 3/1999 | Dossel et al. | | 600/409 |
| 6,009,208 A | 12/1999 | Mitra et al. | | 382/254 |
| 6,086,525 A * | 7/2000 | Davey et al. | | 600/13 |
| 6,104,943 A * | 8/2000 | Frederick et al. | | 600/410 |
| 6,198,958 B1 * | 3/2001 | Ives et al. | | 600/411 |
| 6,266,556 B1 * | 7/2001 | Ives et al. | | 600/544 |
| 6,275,038 B1 | 8/2001 | Harvey | | 324/309 |
| 6,289,234 B1 * | 9/2001 | Mueller | | 600/410 |
| 6,321,105 B1 * | 11/2001 | Jenkins et al. | | 600/407 |
| 6,362,621 B1 | 3/2002 | Miyamoto et al. | | 324/312 |
| 6,370,416 B1 * | 4/2002 | Rosenfeld | | 600/410 |
| 6,477,399 B2 * | 11/2002 | Biswal et al. | | 600/410 |
| 6,697,660 B1 * | 2/2004 | Robinson | | 600/409 |
| 7,087,008 B2 * | 8/2006 | Fox et al. | | 600/13 |
| 2002/0082495 A1 | 6/2002 | Biswal et al. | | 600/410 |

OTHER PUBLICATIONS

Kamei H, Iramina K, Yoshikawa K, Ueno S (1999): Neuronal current distribution imaging using MR. IEEE Trans Magn 35:4109-4111.*
"Magnetoencephalography and magnetic source imaging in children." Otsubo H, Sneed OC 3rd. J Child Neurol Apr. 2001; 16(4):227-35. [Abstract only.].

(Continued)

*Primary Examiner*—Ruth S Smith
*Assistant Examiner*—Joel M Lamprecht
(74) *Attorney, Agent, or Firm*—Trop, Pruner & Hu, P.C.

(57) ABSTRACT

In one embodiment, the present invention includes a method for performing magnetic resonance imaging on a subject and directly mapping electromagnetic activity of neural firing of the subject via the magnetic resonance imaging.

31 Claims, 9 Drawing Sheets

OTHER PUBLICATIONS

"Advantages and limitations of magnetic source imaging." Williamsnon SJ, Lu Zl, Karron D, Kaufman L. Brain Topogr 1991 Winter; 4(2):169-80. [Abstract only.].

"[Insights into Brain Function through Magnetic Source Imaging: A Review of Research and Clinical Aplications] [Article in Spanish]" Simos PG, Papanicolaou AC, Castillo EM, Breier JI, Fletcher JM, Wheless JW, Maggio WW, Constantinou JE. Rev Neurol May 1, 2002; 34(9):871-6. [Abstract only.].

"Magnetic source imaging and brain surgery: presurgial and intraoperative planning in 26 patients." J Neurosurg Jan. 2000; 92(6):1079-80. [Abstract only.].

"Magnetic source imaging guidance of gamma knife radiosurgery for the treatment of epilepsy." Smith JR, King DW, Park YD, Lee MR, Lee GP, Jenkins PD. J Neurosurg Dec. 2000; 93 Suppl 3:136-40. [Abstract only.].

"Mapping of expressive language cortex using magnetic source imaging." Castillo EM, Simos PGB, Venkataraman V, Breier JI, Wheless JW, Papanicolaou AC. Neurocase 2001; 7(5):419-22. [Abstract only.].

"Toward Direct Mapping of Neuronal Activity: MRI Detection of Ultraweak, Transient Magnetic Field Changes" Jerzy Bodurka and Peter A. Bandettini. Feb. 4, 2002. Magnetic Resonance in Medicine (2002), 47:1052-1058.

"Brain activation profiles in dyslexic children during non-word reading: a magnetic source imaging study" Panagiotis G. Simos, et al. Oct. 21, 1999. Neuroscience Letters 290 (2000); 61-65.

"Cerebral Mechanisms Involved in Word Reading in Dyslexic Children: a Magnetic Source Imaging Approach" P. G. Simos, et al. Aug. 2000. Cerebral Cortex; 10:809-816.

"Functional Brain Mapping with Magnetoencephalography" Papanicolaou, A. C. The Neuroscience Research Center Newsletter; vol. 6, No. 1, 1999. http://nba19.med.uth.tmc.edu/nrc/newsltr/.

"Recent Advances in Magnetic Resonance" Narayana, P. A. The Neuroscience Research Center Newsletter; vol. 6, No. 1, 1999. http://nba19.med.uth.tmc.edu/nrc/newsltr/.

"Epilepsy: New Technologies Aid in Diagnosis and Treatment" Wheless, James. The Neuroscience Research Center Newsletter vol. 5, No. 1, 1998. http://nba19.med.uth.tmc.edu/nrc/newsltr/.

"Magnetic Source Imaging in Stereotactic and Functional Neurosurgery" Orrison, Jr. W. W., Meet An Soc Stereotact Funct Neurosurg, Snowbird, Utah, 1999. Stereotact Funct Neurosurg 1999: 72:89-94.

PCT/US03/29035 International Search Report, Mailed Jun. 15, 2004.

PCT/US03/29035 Written Opinion Mailed Sep. 22, 2005.

* cited by examiner

USING MAGNETIC RESONANCE IMAGING TO DIRECTLY MAP NEURONAL ACTIVITY

This application claims priority to U.S. Provisional Application No. 60/412,171 filed on Sep. 20, 2002 in the names of Jinhu Xiong, Jia-Hong Gao, and Peter T. Fox, entitled "Using Magnetic Resonance Imaging to Directly Map Neuronal Activity".

BACKGROUND

The present invention relates to medical imaging and more specifically magnetic resonance imaging (MRI).

Various neuroimaging techniques are presently available. These techniques include MRI, functional MRI (fMRI), and positron emission tomography (PET), for example. None of these techniques, however, are able to directly measure neural activity, i.e., brain activity.

Instead, these techniques detect brain activity via cerebral hemodynamic and metabolic responses to neural firing. However the temporal resolutions of fMRI and PET are ultimately limited by the slow response function of cerebral hemodynamics, which is on the order of seconds. Furthermore, their inferences regarding neuronal activity are necessarily complicated by the variability of coupling between neuronal activity, cerebral hemodynamics, and metabolism.

Other techniques to map neural activity include electroencephalography (EEG) and/or magnetoencephalography (MEG). However, these techniques often have poor spatial resolution. Because both EEG and MEG rely on information detected at the scalp to localize active sites inside the brain, both EEG and MEG require solving an inverse problem, which leads to spatial uncertainty in the localization of electromagnetic sources. In addition, EEG and MEG are each limited in the activation geometries they can detect and are unable to detect neuronal activities deep in the brain. While combining information from modalities detecting different physiological variables (for example, data from fMRI and MEG) can partially offset the drawbacks of the individual modalities and can provide brain activation maps with high spatial and temporal resolution, the basic limitations for each modality, such as the indirect nature of fMRI measurement and the inverse problems for EEG and MEG, remain obstacles.

Thus a need exists to provide improved combined spatio-temporal resolution of neural activity imaging. Further, a need exists to directly map such neural activity to avoid the inverse problem, and directly measure magnetic sources originating from neural firing with high spatio-temporal resolution.

SUMMARY OF THE INVENTION

Functional operations of the human brain are 4-dimensional (4D) processes (i.e., time and space). Even simple tasks activate neural populations distributed across the brain in space and time, which can be fully mapped only by techniques with high spatio-temporal resolution.

Embodiments of the present invention include methods and apparatus to directly map neural activity using MRI. As used herein the terms "directly mapping" or "direct mapping" mean the measurement of neural activity concurrently with neural electromagnetic changes. That is, in contrast to other techniques in which such neural activity may be inferred or measured via cerebral hemodynamic and metabolic changes (incurring a temporal delay), "directly mapping" means the measurement of electromagnetic effects of neural activity without a temporal delay and without a need for solving an inverse problem. This direct mapping may be referred to herein as "magnetic source MRI" (msMRI). In so doing, system-level, event-related neuronal activity may be mapped with high spatial and temporal accuracy by directly detecting magnetic transients induced by neural firing. Further, via such temporal accuracy, latency for activation to spread from location to location may be measured. Such latency may include absolute latency (e.g., relative to a delivered stimulus); and inter-regional latency (i.e., signal travel time between brain regions). Such measurements of intracerebral latencies may be used to model neural system and may aid in diagnosis and study of brain disorders.

Embodiments of the present invention may be used to greatly increase the temporal resolution with which MRI can map brain functional activity and provide a powerful new tool for mapping brain functional organization in humans and animals.

Further still, embodiments of the present invention may be used to detect intrinsic rhythms within the nervous system. That is, in accordance with the present invention, embodiments may detect intrinsic brain oscillations which may be present in the absence of perturbations. In so doing, changes in intrinsic rhythms over time may be measured and analyzed. These changes may be used to indicate various states of nervous system functionality. For example, such changes in rhythm may relate to brain damage, drug effects, and or nervous system disease/disorders.

In other embodiments, similar analyses of nervous system state may be accomplished by use of msMRI in connection with a mental event. As used herein the term, "mental event" means any externally or internally caused activation, perception, cognition, emotion and or attention. Further, as used herein the term "event related" may mean both block design activities in which multiple stimuli are presented and measured, and event related activities in which a stimulus is provided and a series of measurements are then made.

Further still, in certain embodiments, msMRI may be conjoined with one or more other measurements of nervous system state. For example, msMRI may be performed in connection with fMRI to measure cerebral hemodynamic, metabolism and/or neuronal activity. Similarly, msMRI may be performed in connection with EEG or MEG. In yet other embodiments, msMRI may be combined with other imaging techniques, such as PET, computed tomography (CT), or single-photon computed tomography (SPECT), for example. In so doing, metabolic, hemodynamic, and electromagnetic activity of the nervous system may be measured.

By using embodiments of the present invention, co-variants between different neural sites may be measured and analyzed. Such co-variants may be used in diagnosis of disease or disorders of the nervous system, as well as the analysis of drug effects and analysis of anatomical connectivity between neural sites.

In one embodiment, the present invention may include detecting, using MRI, regional neural activity in a subject undergoing MRI scanning, based on magnetic fields induced by the regional neural activity; and spatially and temporally localizing the neural activity using at least a portion of the detected magnetic fields.

DETAILED DESCRIPTION

In one embodiment, mapping brain activity with MRI by detecting magnetic fields induced by neural firing may be accomplished by inducing and detecting phase coherent signals of proton nuclear spins. Neuronal activity creates ionic currents which induce weak electromagnetic fields ($\sim 10^{-13}$ Tesla (T)). Nuclear spins exposed to neuronally induced magnetic fields will lose phase coherence, which will slightly decrease MRI signal strength. Neuronal magnetic transients may be mapped, therefore, by detecting event-related decrements in the MRI signal.

Figure 1:
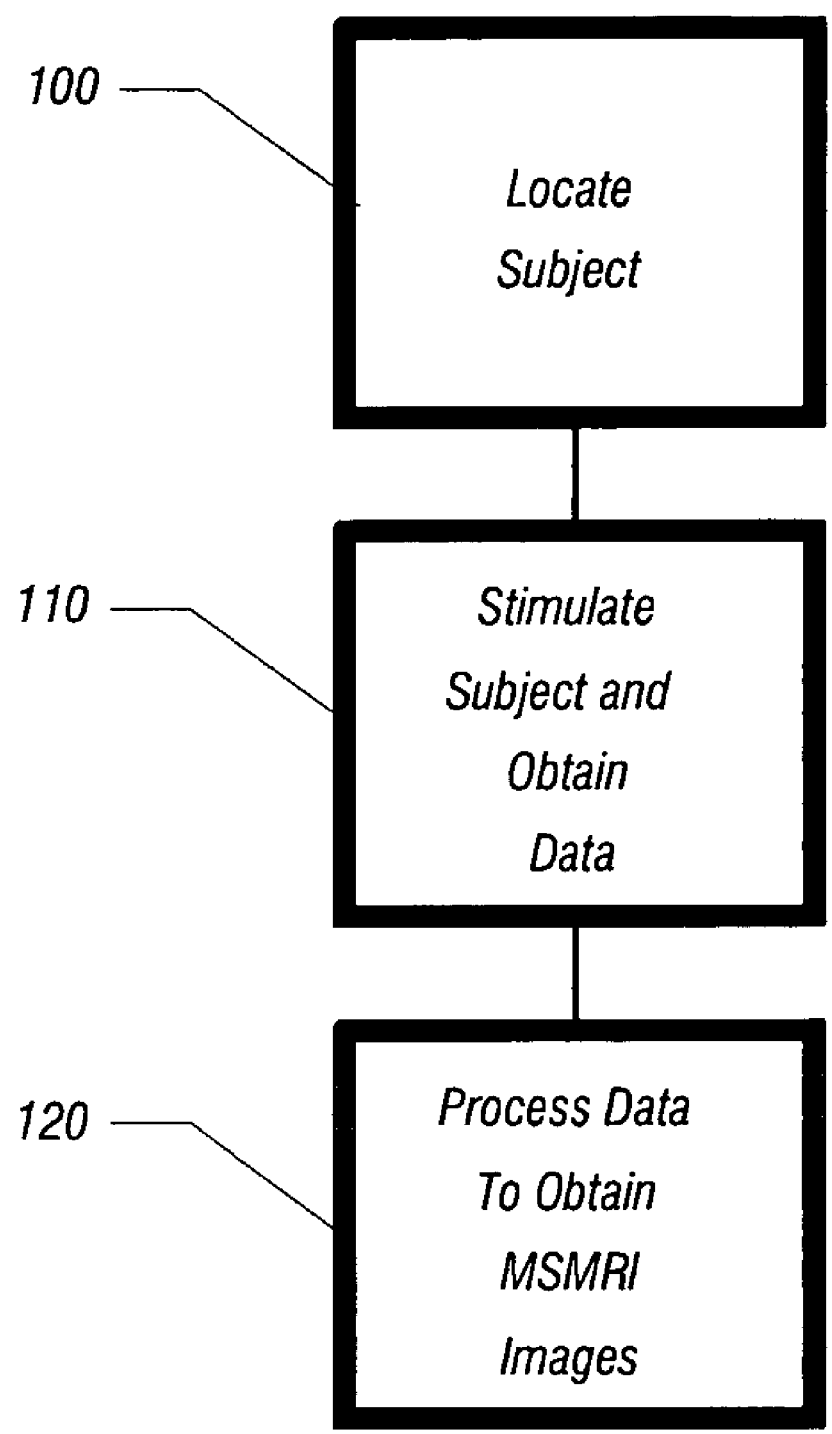
FIG. 1 is a flow chart of an example method according to the present invention.

Referring now to FIG. 1, shown is a flow chart of an example method according to the present invention. As shown in FIG. 1, the method begins with the location or placement of a subject within an MRI scanner (block 100). It is to be understood that any MRI scanner may be used in connection with the present invention. As is well known in the art, such subject location may place the subject in an RF coil. Furthermore, the MRI magnets may be shimmed to the subject. Furthermore, within block 100 it is to be understood that other well known techniques in the initialization of MRI scanning may be performed, such as preparing a scout image.

Next, the subject is stimulated and data is obtained (block 110). While not shown in FIG. 1, it is to be understood that obtaining data and stimulating the subject may be performed iteratively, as desired by a particular msMRI procedure. While it is to be understood that in certain embodiments, the stimulation may be an external stimuli such as a task (e.g., visuomotor task), in other embodiments, the stimuli may be internally provided. Further still, in other embodiments, no stimuli need be presented, and msMRI may measure intrinsic rhythms of the nervous system in the absence of stimuli. Data is obtained in accordance with well known MRI techniques. The data obtained may include, for example, information regarding transient magnetic fields. Information of transient magnetic fields may be obtained by measuring MRI signal changes in magnitude or phase. In certain embodiments the data obtained may relate to MRI signal magnitude. Because orientations of neuronal currents are very complex and pseudo-random, phases may destructively add, resulting in a minimal phase shift and a large phase dispersion. Magnitude measurements, therefore, may be more sensitive for measuring the collective neuronal activity than phase measurements.

Finally, data processing is performed to obtain the desired msMRI images (block 120). Such processing may be performed in accordance with well known MRI techniques in which images are reconstructed from the data obtained using a data analysis machine. In certain embodiments the data analysis machine may be data processing system, such as a personal computer, workstation, or the like. The data processing typically includes multiple steps, for example, image reconstruction, motion correction, spatial normalization, value normalization/correction, statistical analysis, and statistical inference.

Various data processing techniques may be used to analyze the images. For example, various image reconstruction methods may be performed to obtain desired images from the MRI signal. Various motion corrections may be performed to minimize image artifacts related to subject movements. Various spatial normalization procedures may be performed to standardize the size, position, and orientation of images across different subjects. Various value normalization/correction methods may be performed to minimize the physical and physiological artifacts of the MRI signal acquired over time. Various statistical analyses may be performed to create different statistical parametric images such as z-, t-, or r-images.

In certain embodiments, the data processing techniques may be implemented in software. As such, these embodiments may be stored on a storage medium having stored thereon instructions which can be used to program a data processing device, such as a computer system or the like, to perform the embodiments. The storage medium may include, but is not limited to, any type of disk including floppy disks, optical disks, CD-ROMs, CD-RWs, and magneto-optical disks, semiconductor devices such as ROMs, RAMs, EPROMs, EEPROMs, magnetic or optical cards, or any type of media suitable for storing electronic instructions. Similarly, embodiments may be implemented as software modules executed by a programmable control device. A programmable control device may be a computer processor or a custom designed state machine, for example.

It is to be understood that various MRI pulse sequences may be used. In various embodiments of the present invention, an asymmetric pulse sequence may be used. Such an asymmetric pulse sequence may be used to avoid cancellation of the signal by the second pulse in the pair. In one embodiment, a gradient-echo echo-planar-image (EPI) pulse sequence may be used. In various embodiments, the asymmetric pulse sequence may have a repetition time of between approximately 40 and 10,000 milliseconds, an echo time of between approximately 10 and 200 milliseconds, and a flip angle of between approximately 10 and 180 degrees. More specifically, in certain embodiments, the pulse sequence may include a repetition time of between approximately 400 and 4,000 milliseconds, an echo time of between approximately 50 to 150 milliseconds, and a flip angle between approximately 40 to 120 degrees. However in other embodiments, other parameters may be used. Further in other embodiments, other pulse sequences such as a conventional spin echo, gradient echo, fast spin echo, spin-echo EPI, or a spiral imaging pulse sequence may be used.

In certain embodiments, a hemodynamically neutral msMRI technique may be used. Brain activity induces large hemodynamic effects (e.g., increased blood flow). These hemodynamic effects are slow but strong. Generally, they reach a peak only after 4 to 6 seconds and decline equally as slowly. Thus as used herein the term "hemodynamically neutral" means the obtaining of data during a time in which hemodynamic effects are at a substantial steady state.

Figure 2:
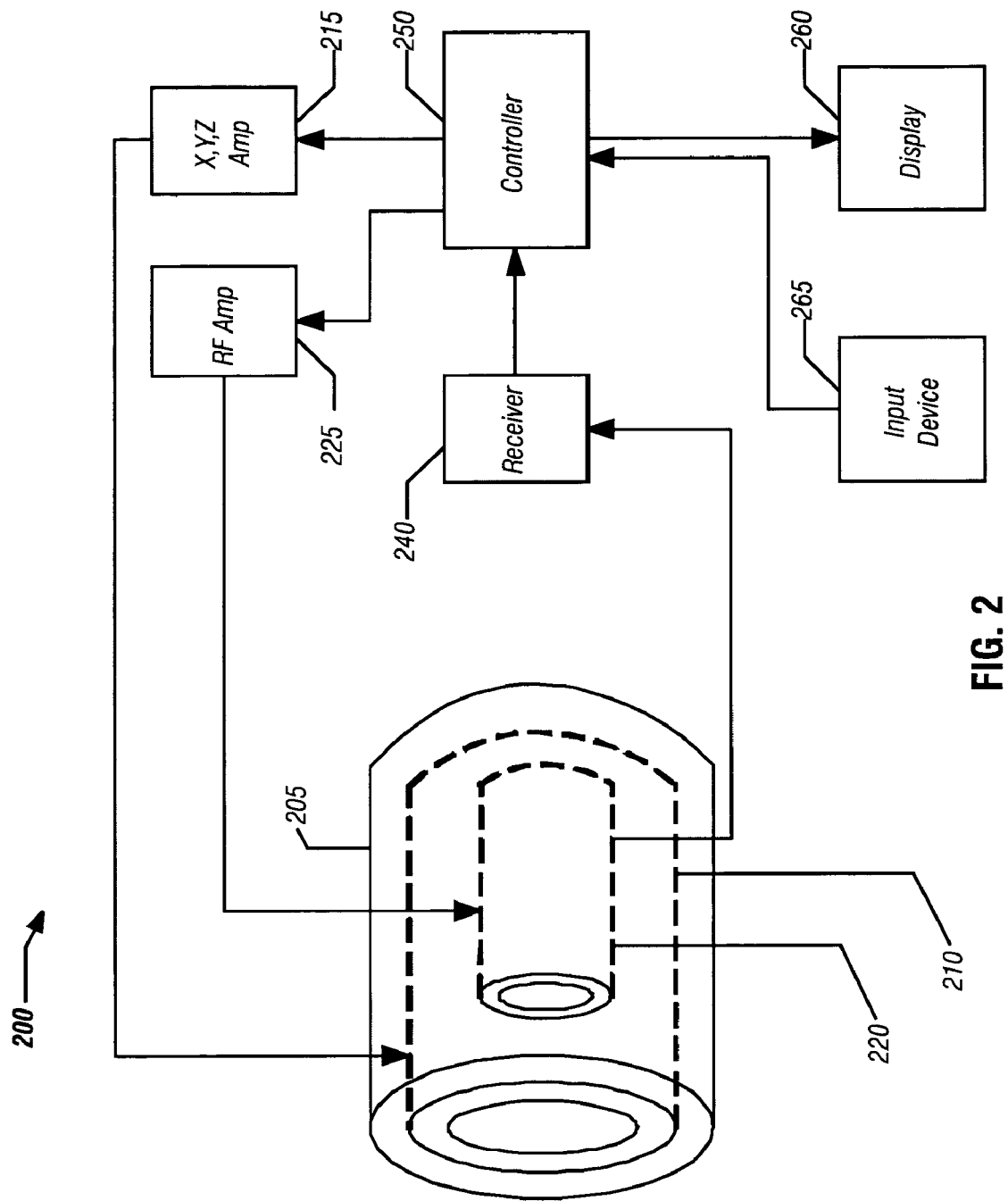
FIG. 2 is a block diagram of a MRI system in accordance with an embodiment of the present invention.

Referring now to FIG. 2, shown is a block diagram of an MRI system in accordance with an embodiment of the present invention. As shown in FIG. 2, system 200 includes an MRI scanner 205 having a gradient coil 210 and an RF coil 220. Shown in FIG. 2, the gradient coil 210 may be controlled via x, y, z amplifier 215, while the RF coil 220 may be controlled via an RF amplifier 225. While shown as including such coils, it is to be understood that FIG. 2 is shown for illustrative purposes and an MRI scanner in accordance with an embodiment of the present invention may include additional components of a standard scanner such as a main magnet, additional gradient magnets, and the like.

The amplified signals provided by MRI scanner 205 may be provided under control of a controller 250. In one embodiment, controller 250 may be a workstation, server, personal computer or other data processing system capable of providing control signals for system 200.

Coupled to controller 250 may be a display 260 and an input device 265 for providing display information regarding an MRI process and to receive input information from a user, respectively. More so, a receiver 240 may be coupled to MRI scanner 205 to receive resonance signals therefrom and preprocess them. As shown in FIG. 2, received resonance signals may be provided from receiver 240 to controller 250 for further processing. Alternately, such resonance signals may be provided to a separate data processor for desired processing.

In accordance with an embodiment of the present invention, controller 250 may include software routines and the like to obtain msMRI signals and use them to map neural activity with a high degree of spatial and temporal localization.

While shown with the specific components discussed above in FIG. 2, it is to be understood that embodiments of the present invention may be used with various MRI devices now known or available in the future.

Figure 3A:
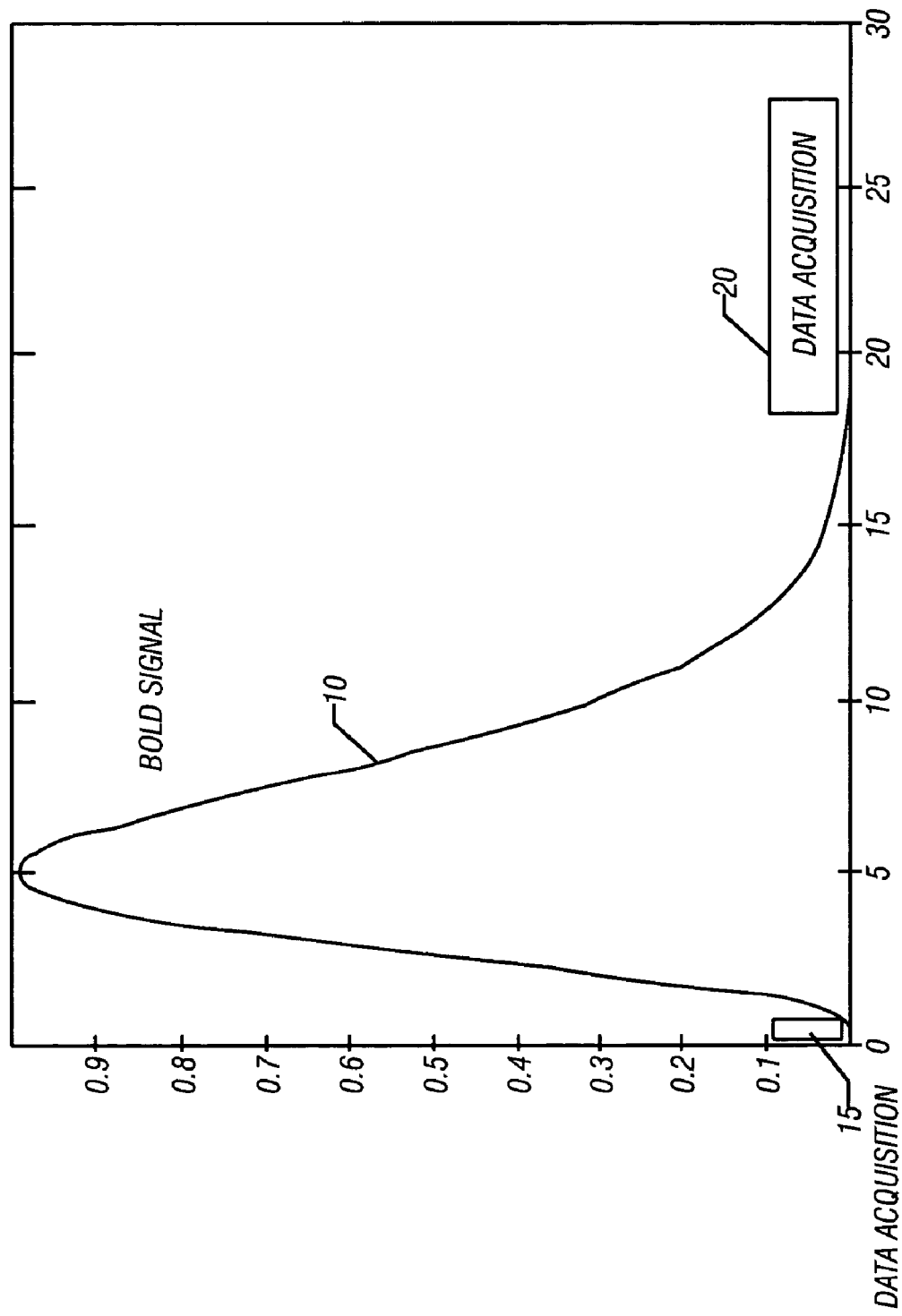
FIGS. 3A and 3B are graphical representations of hemodynamically neutral data acquisitions according to the present invention.
Figure 3B:
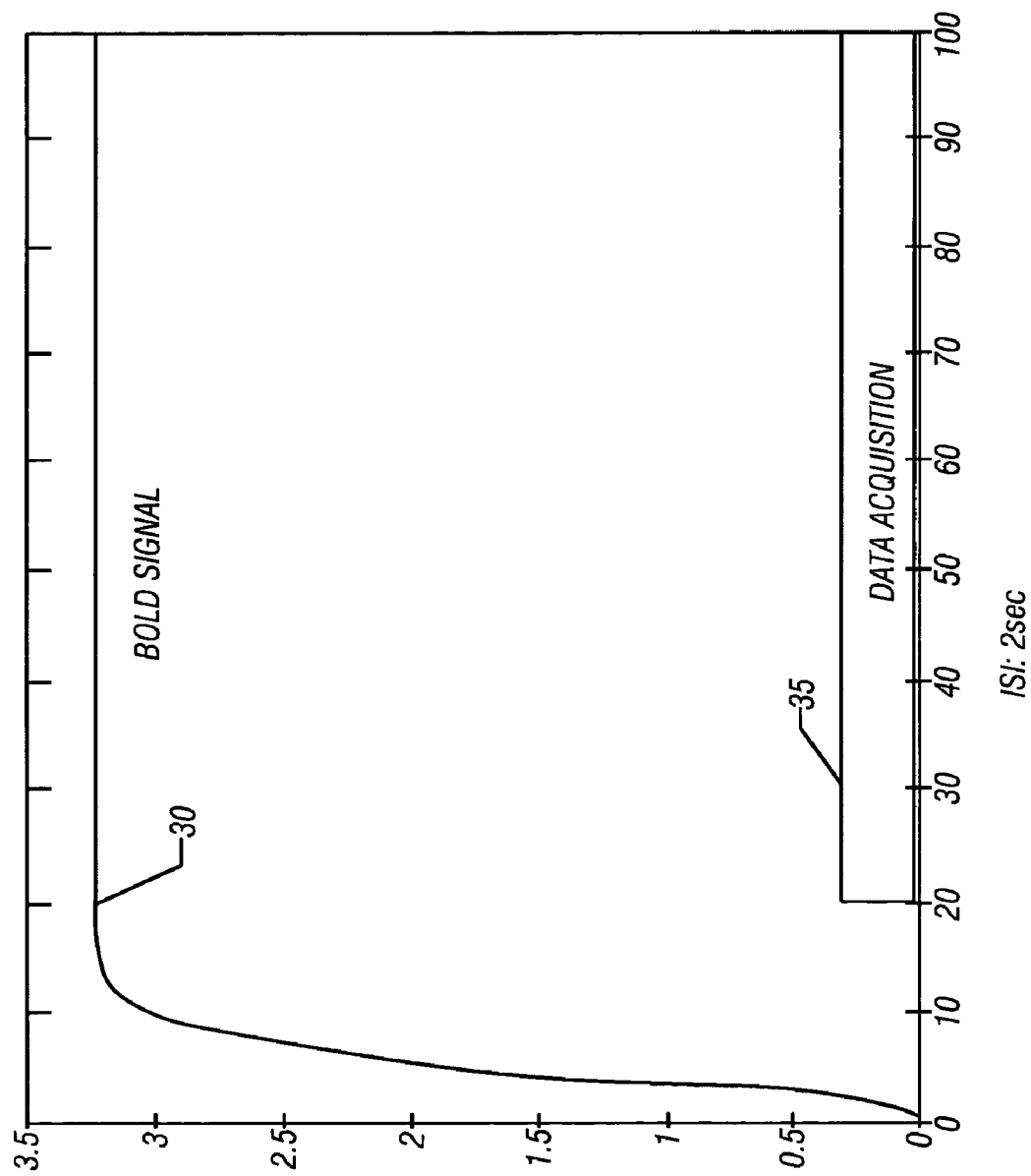

Referring now to FIGS. 3A and 3B, shown are graphical representations of two manners of obtaining a hemodynamically neutral response in accordance with the present invention. As shown in FIG. 3A, a blood oxygen level-dependent (BOLD) signal 10 rises to a peak approximately five seconds after an event. To provide for a hemodynamically neutral analysis, data may be obtained in windows 15 and 20, occurring prior to and after hemodynamic activity. Alternately, in an msMRI technique in which multiple rapid stimuli are provided, the hemodynamic response causes fluxes in brain activity too fast for hemodynamic changes to track. That is, a hemodynamic response plateaus and remains at a steady state throughout the data acquisition. In such a technique, a BOLD signal 30 remains at a substantial steady state, so that data acquisition may occur in window 35, shown in FIG. 3B.

Exemplary Study

In a study according to the present invention using a well-established visuomotor paradigm, human brain msMRI images correctly detected the locations and latencies of activations in visual, motor, and premotor cortices, with a temporal resolution of 100 milliseconds (ms) and spatial resolution of 3 millimeters (mm). Signal strength was comparable to other event-related functional MRI methods: about 1% of the baseline signal.

In this exemplary study, a simple, well-established visuomotor task was used to map the system-level organization of the human motor and visual cortices using msMRI. In the study, the subject's heads were immobilized in a closely fitted, thermally molded, plastic facial mask individually formed for each subject. Such masks minimize head movement during MRI scanning. Cued by a brief (50 ms) stimulus (a wedge of random dots) in the lower left visual field, subjects pressed and released a button with the right index finger. Magnetic source MRI images were acquired over a 1300 ms period starting at 200 ms before cue onset and divided into thirteen consecutive, 100 ms time frames. Six time frames (0-600 ms after cue onset) were reported. Images were spatially configured as five contiguous axial slices with a slice thickness of 6 mm and orientated to cover both the upper bank of the calcarine cortex (the lower field representation of primary visual cortex) and the hand area of primary motor cortex. In plane spatial resolution was 3 mm. A relatively long echo time (TE=100 ms) was used to maximize the strength of the msMRI signal. Six normal subjects (five men and one woman) were scanned. Three of them were scanned twice one week apart to assess reproducibility of brain activation. In addition to msMRI, a high resolution (1×1×1 mm) anatomical MRI and a "traditional" BOLD fMRI were acquired in each subject. The BOLD fMRI was acquired in a block design, using the same visuomotor task and a resting-state control.

Figure 4:
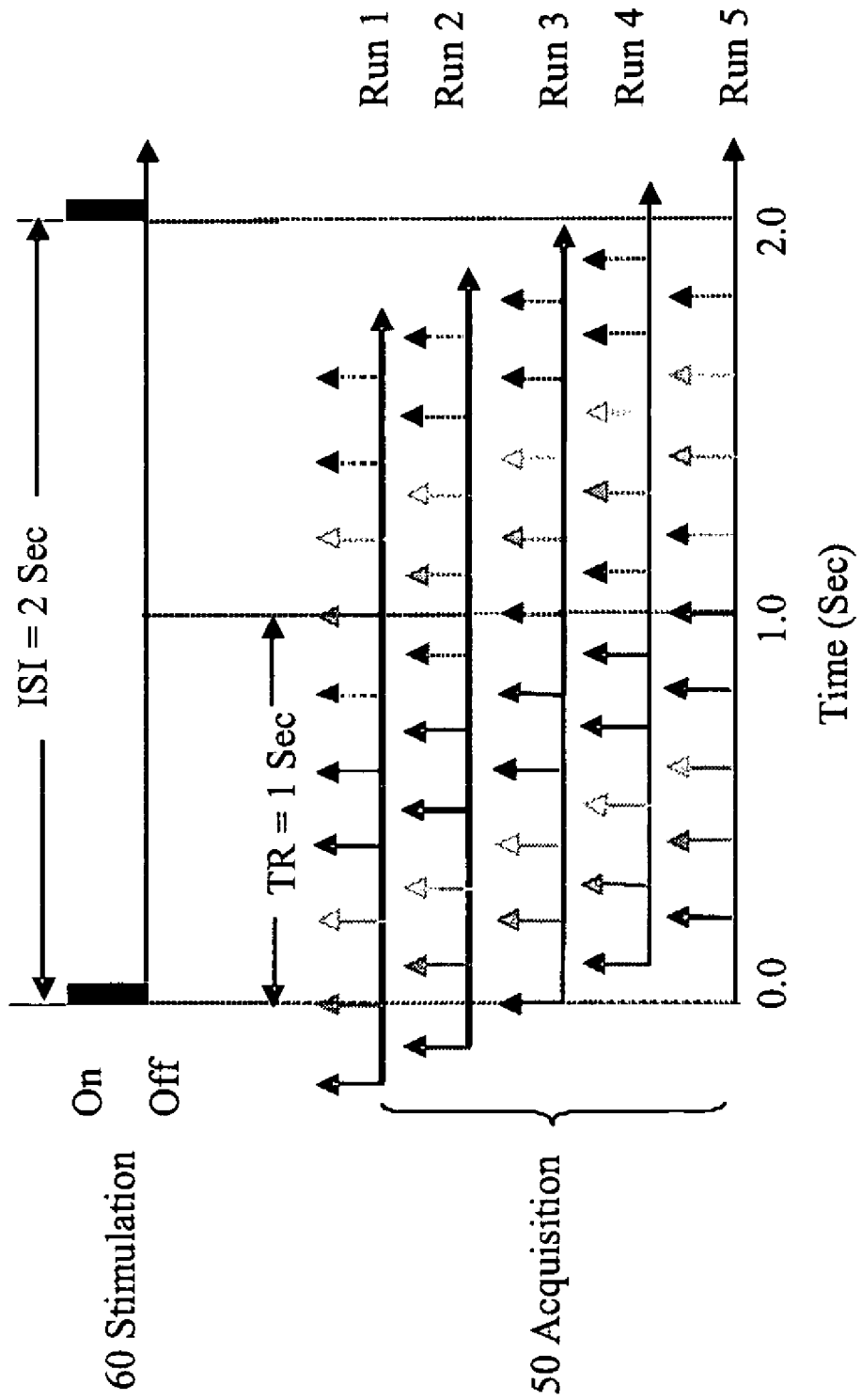
FIG. 4 is a time sequence for an exemplary study in accordance with the present invention.

Referring now to FIG. 4, shown is a time sequence used for the exemplary study. For each stimulation ON/OFF cycle 50, one five-slice image was acquired corresponding to the ON period (solid arrows) and another corresponding to the OFF period (dash arrows). Each slice was color-coded. The time between adjacent slices was 200 ms. The MRI scanner was precisely synchronized with stimulation onset.

As shown in FIG. 4, data acquisitions 60 for the first five runs start at −200, −100, 0, 100, and 200 ms relative to stimulation onset. In this exemplary study, MRI data were acquired on a 1.9 T GE/Elscint PRESTIGE whole-body MRI scanner using a gradient-echo echo-planar-image (EPI) pulse sequence with the following parameters: repetition time, TR, of 1000 ms, echo time, TE, of 100 ms, and a flip angle of 90 degrees.

Five contiguous, oblique slices were acquired, with an in-plane spatial resolution of 3×3 mm$^2$ and slice thickness of 6 mm. The orientation and location of the slices were carefully selected to include both visual and motor areas.

For the exemplary study, each MRI session included six runs of data acquisitions, with an acquisition time of 200 seconds per run. The first five runs were designed for msMRI imaging of event-related neuronal activity and are shown in FIG. 4. Each run consisted of 100 ON/OFF cycles, with two multiple-slice images for each cycle (one inter-stimulation interval (ISI)). The last run was a control. It was acquired either at a resting-state (subject does not actively perform any task) or as a block design conventional blood oxygen level dependent (BOLD) fMRI study, in which subjects performed the visuomotor task for the first 90 seconds and then rested for the rest of time.

Figure 5:
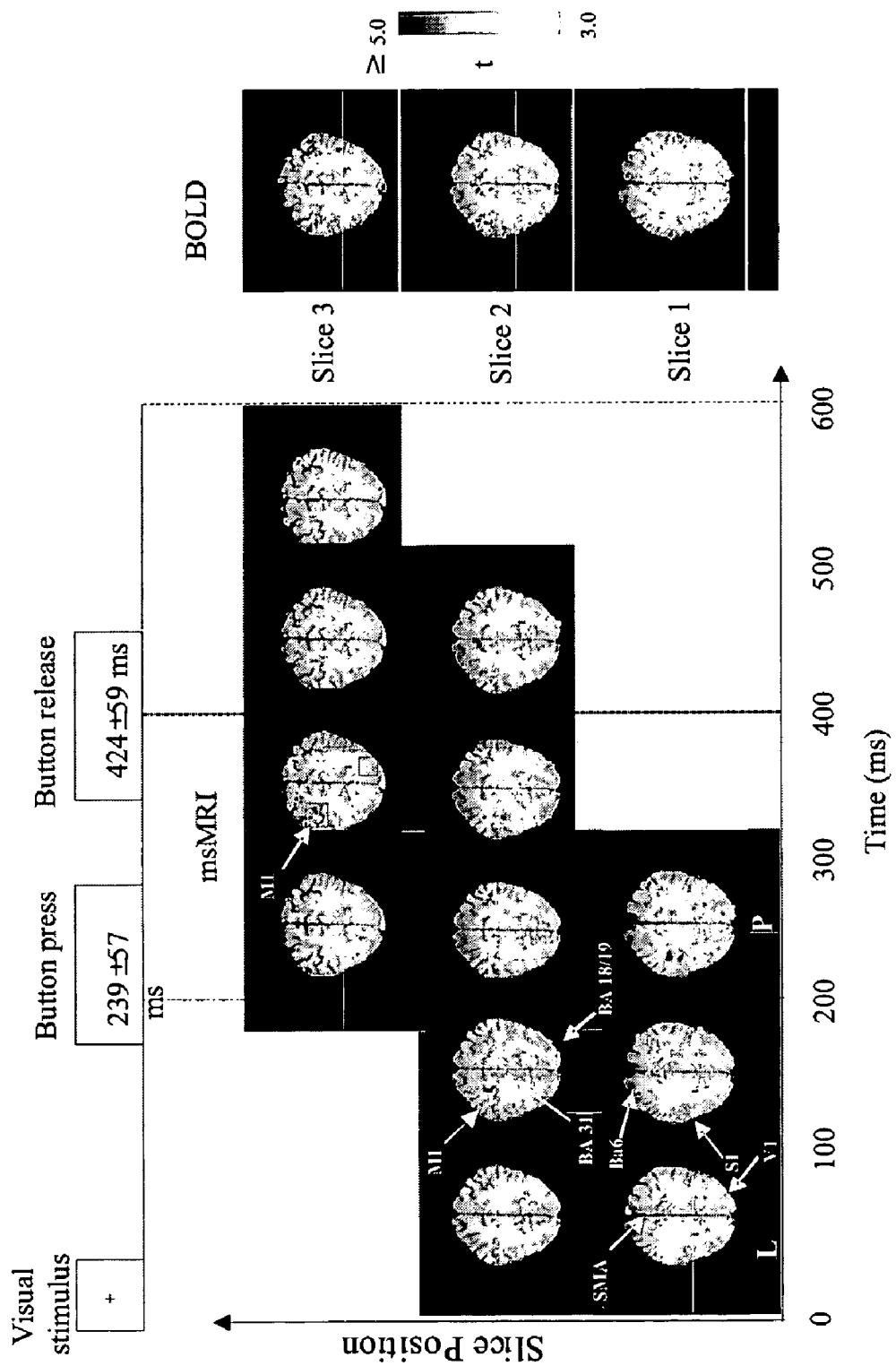
FIG. 5 shows spatio-temporal plots of event-related neural activity of a subject detected by msMRI and BOLD fMRI maps for the subject in accordance with the present invention.

Referring now to FIG. 5 (left side), shown are spatio-temporal plots of event-related neuronal activity detected by msMRI for a single subject in accordance with the exemplary study. For comparison, the same subject's BOLD fMRI maps are also shown in FIG. 5 (right side). The time sequence of visual and motor events is shown along the top of FIG. 5. The activation information is overlaid on T1-weighted MRI images acquired at the same location and orientation. Because different MRI slices were acquired at slightly different times, spatial normalization was not performed to preserve temporal information. The letter L on the left-lower corner indicates the left cerebral hemisphere. The letter P indicates posterior. The term V1 refers to the right striate cortex, S1 refers to the left somatosensory cortex, SMA refers to the anterior supplementary motor area, and M1 refers to the left primary motor and premotor cortices. While not shown in FIG. 5, color images may be used in which a color scale exists to represent the t value of each voxel.

For the exemplary study, the MRI images were processed using image processing software. Several modifications to the software were performed to accomplish this study. For example, motion correction, and value normalization/correction procedures were modified, as discussed above.

In the exemplary study, the first 20 images of each run were discarded to allow hemodynamics and the MRI signal to reach a steady state. All data were assessed for inter-scan, intra-subject movement. A two-dimensional (2D) movement correction was performed to minimize in-plane motion. Data interpolation between image slices was purposely avoided because different slices were acquired at different times. Voxel-by-voxel linear detrending was performed to remove the linear drift of the MRI signal. A mean image was created for each on-off cycle by averaging across the time-series in the cycle; the mean image was then subtracted from each image to create residual images. A 2D spatial Gaussian filter with a full width at half magnitude of 4.5 mm was applied. A group Student's t test was performed on the residual images. The t-image was then thresholded using a t-value threshold of 3.0 ($p<0.0013$) and cluster size threshold of 4 voxels to detect significant activation.

Figure 6:
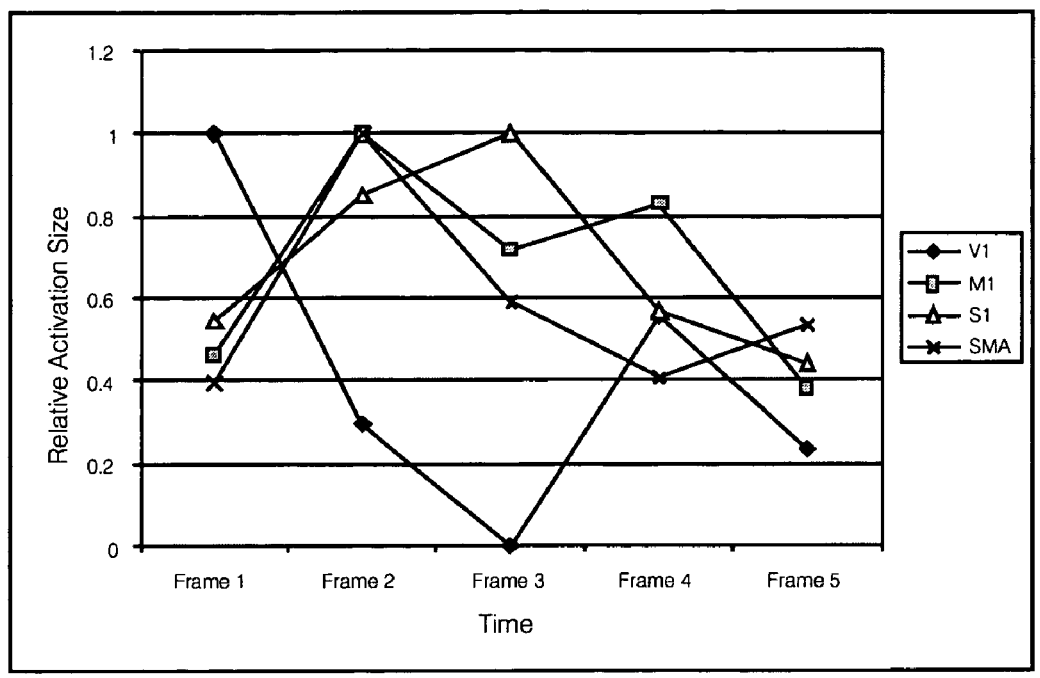
FIG. 6 is a graphical representation of averaged time courses of relative activation sizes in the exemplary study according to the present invention.

Referring now to FIG. 6, shown is a graphical representation of averaged time-courses of relative activation sizes for different brain regions in accordance with the exemplary study. Activation sizes were averaged across subjects and sessions and were normalized by dividing each size with the maximum size for the region. Four different brain regions are shown: the right striate cortex (V1), the left primary motor and premotor cortices (M1), the left somatosensory cortex (S1), and the anterior supplementary motor area (SMA). Time frames 1-5 represent time intervals of 0-100 ms, 100-200 ms, 200-300 ms, 300-400 ms, and 400-500 ms after the visual stimulation onset, respectively.

Figure 7:
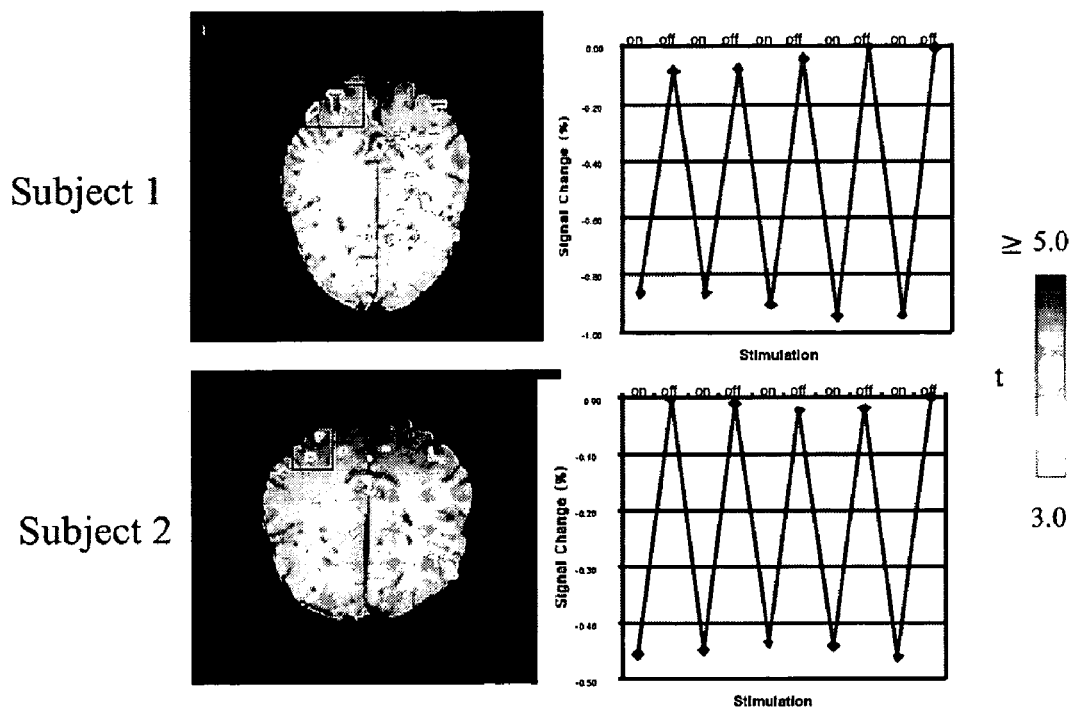
FIG. 7 are functional activation maps and graphical representations of event related signal changes for two subjects in the exemplary study according to the present invention.

Referring now to FIG. 7, shown are functional activation maps and graphical representations of event-related signal changes for two different subjects in accordance with the exemplary study. As shown in FIG. 7, the activation information has been overlaid on T1-weighted MRI images acquired at the same location and orientation. Again, while not shown in FIG. 7, for color images, a color scale may be used to represent the t value of each voxel. The images shown in FIG. 7 are oriented the same as those of FIG. 5. The graphical representations represent signal changes corresponding to the activated areas inside the boxes. Each data point represents an average of 18 individual trials.

A current-dipole model was constructed for modeling MRI signal changes resulting from neuromagnetic fields. The model was constructed over a scale range from a single neuron to a typical MRI voxel (approximately one million neurons). Each dendrite was modeled as a current dipole. Distributions of neuronal magnetic fields were estimated and the interaction between the neuronal magnetic fields and nuclear spins was assessed across a range of scales, orientations, configurations, and distributions of dendrite packing density. More detailed information regarding modeling is discussed below.

As predicted, msMRI detected regional signal decrements in visual, sensorimotor, and pre-motor cortices with appropriate latencies (below), locations, and lateralities. For all subjects, occipital activations bordered the calcarine fissure and were predominately right hemispheric, consistent with the left visual field location of the cue. Similarly, sensorimotor and premotor activations were chiefly left hemispheric, consistent with the right-hand motor response. Primary motor area (M1) responses lay immediately anterior to the central sulcus; primary sensory cortex (S1) responses lay immediately posterior to the central sulcus. The locations of task-induced activations detected by msMRI and BOLD fMRI were in good agreement in all subjects. In the illustrated subject of FIG. 5, locations and lateralities of msMRI activations in M1, S1, the supplementary motor area (SMA) and posterior cingulate were closely replicated by BOLD fMRI.

In all areas imaged, msMRI signals were detected predominately in cerebral grey matter, as shown in FIG. 5. Grey matter localization of msMRI signals may appear counter-intuitive, but is in good agreement with known electrophysiology.

In addition to accurate spatial information, msMRI maps provided richly detailed temporal information regarding task-induced neuronal activity. As illustrated in FIG. 5 (single subject) and FIG. 6 (group data), msMRI maps showed right-hemispheric activation of primary visual (striate) cortex (V1) in frame 1 (0-100 ms) immediately after visual stimulation onset (FIG. 5). The visual activation moved laterally to the right extrastriate visual areas (Brodmann area [BA] 18 and 19) in frame 2 (100-200 ms). Both the striate and extrastriate visual cortical areas were re-activated in frame 4 (300-400 ms). Onset latencies of msMRI visual activations agree well with known EEG onset latencies. Re-entrant activation of visual cortex has also been reported, with onset at 250-300 ms, about 50 ms earlier than the present study. Note that msMRI measures integrated activation within a frame (100 ms). Activation starting late in a frame may not be detected until the subsequent frame, which may explain why activation onsets from EEG are sometimes shorter than those from msMRI. The visual activation patterns illustrated in FIG. 5 were fairly consistent across subjects and sessions. Group data clearly showed the same activation-reactivation patterns with the similar latencies (FIG. 6).

In the motor system as well, msMRI detected activation spatially and temporally discrete and appropriate to the task. In the illustrated subject of FIG. 5, the left primary motor (M1) and premotor areas (BA 6) were activated twice: first in frame 2 (100-200 ms) and then in frame 4 (300-400 ms). Similar activation patterns and onset latencies were observed in the group data (FIG. 6). The first M1 activation is likely preparation for and execution of the button press. Using a similar visuomotor task, onset latencies of 130-180 ms for motor and premotor cortices have been reported, in excellent agreement with the present study. The second M1 activation likely represents the same components for button release. Chronometric measurements showed an average delay of 185 ms between button press and button release, which closely matches the delay between the first and second M1 activations. As expected, the onset of brain activation preceded finger movement by about 100 ms (finger response time: 239±57 ms).

As shown in FIG. 5, primary somatosensory (S1) cortex activation (0-100 ms) preceded M1 activation, and continued during M1 activation (100-200 ms), but reached maximum after M1 activation (200-300 ms). Similar activation patterns and onset latencies were observed in the group data (FIG. 6). Judged by latency, the strongest S1 activation likely reflects the sensory feedback from the finger movement. Left S1 was activated again during the button release period (at 300-400 ms) (FIG. 5). Also activated significantly was the anterior supplementary motor area (SMA) (BA 6), which activated first in frame 1 (0-100 ms), reached maximum in frame 2 (100-200 ms), and continuously activated in frame 3 (200-300 ms), frame 4 (300-400 ms), and frame 5 (400-500 ms) (FIGS. 5 and 6). The posterior cingulate (BA 31) was activated first in frame 1 (0-100 ms) and again in frame 3 (300-400 ms) (FIG. 5). These cingulate activations likely correspond to the Bereitschaftpotential.

The consistency of msMRI in detecting neuronal activity was assessed across subjects and sessions. For all subjects, background noise level in the control studies (the resting state) was very low and no false-positive activations were detected. Trial-by-trial consistency was excellent (FIG. 7), with a clear distinction between baseline and activation. Visual inspections of activation maps showed good consistency across subjects and sessions. For example, for the two subjects shown in FIG. 7, the locations of activations in M1, S1, premotor, SMA, and posterior cingulate cortices are quite similar. In this study, quantitative assessments of activation location variability were not performed, as this requires a much larger sample size and requires spatial normalization.

Data according to the present study contradict the prediction that the magnitude of msMRI signals in the human brain would be very weak. Specifically, in the present study, msMRI signals are similar in magnitude to event-related BOLD fMRI (~1%). For example, the average magnitude (n=6) of the msMRI signal in left M1 cortex was 1.12%±0.54% of the background anatomical signal (FIG. 7). At the same field strength (1.9 T), event-related BOLD fMRI effects have been reported at ~1% of the background signal. The BOLD fMRI protocol, however, used an echo time (TE) of 45 ms, as compared to 100 ms TE for the present study. Functional MRI signal changes are TE dependent, with longer TE yielding larger percentage signal changes.

In various embodiments in accordance with the present invention, a long TE may provide for increased magnitude of msMRI signal strength. In certain embodiments, the TE may be between approximately 10 to 200 ms, and more specifically between approximately 50 to 150 ms.

Further contributing to increased magnitude msMRI signals in certain embodiments may be the measurement of MRI signal magnitude change rather than MRI signal phase change. Because orientations of dendrites are very complex and pseudo-random, phases may destructively add, resulting in a minimal phase shift and a large phase dispersion. Thus in certain embodiments, magnitude measurements may be used. In such embodiment, these measurements may be more sensitive for measuring the collective neuronal activity than phase measurements.

The neuronal activity which induces transient magnetic fields detectable by msMRI may also cause cerebral hemodynamical changes in the surrounding brain tissues. In various embodiments, effects of cerebral hemodynamics may be sought to be minimized, while maximizing the effects of the transient magnetic fields. In the present study, the stimulation ON/OFF cycle was switched rapidly so that the cerebral hemodynamical response was effectively in steady state. The hemodynamically based BOLD signal, therefore, was effectively constant during stimulation ON and OFF phases.

In the present study, the temporal resolution of msMRI is equal to the echo time (TE), 100 ms for the present study. This temporal resolution is desired, but not optimal, to investigate neuronal activity at the system level. Activation of a neural population generally lasts tens to hundreds of milliseconds. Similarly, latencies of activations are also in a range of tens to hundreds of milliseconds. Thus, improving the temporal resolution of msMRI may be desired in certain embodiments. The temporal resolution of msMRI is mainly limited by contrast-to-noise ratio, which is affected by MRI parameters including field strength, repetition time (TR), and echo time (TE), as well as by the pattern of neural firing. Temporal resolution may be further improved by optimization of experimental design and MRI pulse sequences, in certain embodiments.

To confirm that the signals detected by embodiments of the present invention are the direct effects of neuronal magnetic fields, theoretical modeling was performed and experimentally confirmed. A current-dipole model, commonly used in MEG for the estimation of the magnetic fields induced by neuronal firing, was constructed over a scale range from a single neuron to a typical MRI voxel (approximately one million neurons). In the range of parameters proper for human cortex, modeling showed that changes in the magnitude of the MRI signal due to neuronal activity could reach a few percent (0.5% to 5%). That is, msMRI signals in accordance with one embodiment of the present invention are within a measurable range, comparable to standard fMRI techniques.

Figure 8:
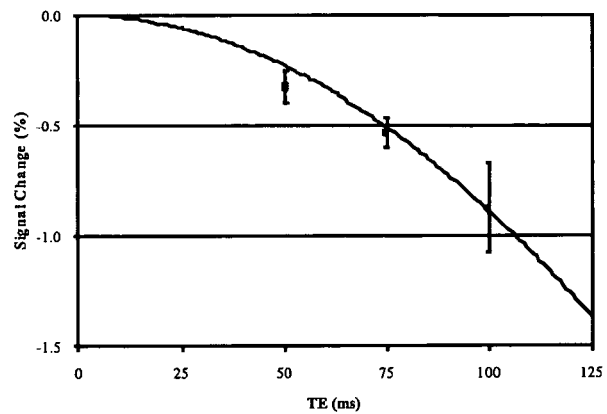
FIG. 8 is a graphical representation of signal change versus echo time in accordance with one embodiment of the present invention.

Referring now to FIG. 8, shown is a graphical representation of percentage of signal change versus echo time. The solid line represents theoretical results, which will be discussed below. The points on the vertical lines represent experimental data, which represent the msMRI signals averaged across all significantly activated legions and across a group of three subjects, where the arrow bars represent one standard error. In the study, the parameters used for calculating the MRI signal changes are: radius of the dendrites $a=0.5$ μm, electrical conductivity of axoplasma $\sigma_i=2\ \Omega^{-1}m^{-1}$, and membrane potential $\Delta v_i=75$ mV. The number of dendrites fired simultaneously at any time was presumed to be approximately 0.2 million for a typical MRI voxel. This theoretical prediction was confirmed by the experimental data, which showed a signal change of 1.12%±0.54% of the background anatomical signal in the left M1 cortex. Response magnitudes for other brain regions were similar.

Modeling also tested the relationship between the msMRI signal strength and the echo time (TE). A counterintuitive prediction of the model is that a nonlinear relationship exists between TE and msMRI magnitude: msMRI signal increased by a factor of 3.8 when TE doubled. This is in sharp contrast to a nearly linear relationship between TE and BOLD fMRI signal. The predicted nonlinearity was experimentally confirmed, as shown in FIG. 8, which is a reason why a long TE for msMRI may be desired.

For neuronal magnetic fields, the direction of the field on the left side of a current dipole is always opposite to that on the right. A typical MRI voxel contains approximately one million dipoles. Both positive and negative phases of MRI signals will destructively add, lowering net phase for an imaging voxel. Thus, the net phase is near zero and is undetectable. On the other hand, magnitude of MRI signal significantly changes due to this neuromagnetic field. Even though millions of dendrites are synchronously activated, the combined magnetic field remains highly inhomogenous. Nuclear spins experiencing these local field inhomogeneities will lose phase coherence, resulting in a decrease of MRI signal magnitude. Magnitude measurements used in accordance with an embodiment of the present invention may thus be far more sensitive for measuring in vivo neuronal activity than phase measurements. In addition to electromagnetic effects, neuronal activity also induces physiological (e.g., changes in blood flow and metabolic rate) and mechanical (e.g., cell swelling) effects.

Thus, spatially and temporally precise signals detected using a model-based experimental design optimized to detect neuronal magnetic effects are, in fact, msMRI effects. The msMRI activations showed a spatial and temporal distribution appropriate to the neural systems activated by the widely used visuomotor task. The sign and magnitude of the observed signals (about −1% of baseline) were as predicted by the model. The nonlinear effect of TE on the observed signal was as predicted by the model. Further, non-magnetic effects of neuronal activity have been addressed but found wanting as explanations of the observed effect.

Techniques in accordance with an embodiment of the present invention offer several advantages over current neuroimaging methods. It appears to provide better combined spatio-temporal resolution than any currently used non-invasive neuroimaging methods. Compared with "traditional" fMRI and positron-emission tomography (PET), msMRI offers much higher temporal resolution, with no loss of spatial resolution. As discussed above, detecting brain activity via the cerebral hemodynamic and metabolic responses to neural firing, the temporal resolutions of fMRI and PET are ultimately limited by the slow response function of cerebral hemodynamics, which is on the order of seconds. Furthermore, their inferences regarding neuronal activity are necessarily complicated by the variability of coupling between neuronal activity, cerebral hemodynamics, and metabolism. Compared with EEG and MEG, msMRI offers higher spatial accuracy. Relying on information detected at the scalp to localize active sites inside the brain, both EEG and MEG require solving an inverse problem, which leads to spatial uncertainty in the localization of electromagnetic sources.

In contrast msMRI effects in accordance with one embodiment of the present invention are spatially mapped in the same manner as traditional MRI techniques and involve no inverse problem. In addition, EEG and MEG are each limited in the activation geometries they can detect and are unable to detect neuronal activities deep in the brain; msMRI has no such limitation. Combining information from modalities detecting different physiological variables (for example, data from fMRI and MEG) can partially offset the drawbacks of the individual modalities and can provide brain activation maps with high spatial and temporal resolution. However, the basic limitations for each modality, such as the indirect nature of a fMRI measurement and the inverse problems for EEG and MEG, remain obstacles. In contrast, msMRI overcomes these limitations and directly measures magnetic sources originating from the neural firing with high spatio-temporal resolution.

As discussed above, modeling has been performed that confirms the results described herein. A neuron in the brain typically consists of a single axon and multiple dendrites. Each dendrite or unmyelinated axon may be modeled using a current dipole model. In such a current dipole model, the current flowing inside a neuron is opposite to the current outside the neuron. The dipole model considers effects of intracellular current $i_i$ and extracellular current $i_e$ and ignores the effect of through membrane current. It can be easily demonstrated that the through membrane current generates no net magnetic field outside neuronal membrane and can be ignored. For myelinated axons, the majority of neural current concentrates at nodes of Ranvier and is through membrane current. Contributions of a myelinated axon to overall magnetic field are small and can then be ignored. As the majority of axons in the brain are myelinated, dendrites are the main source of neuronal magnetic fields.

Magnetic field generated by a current dipole at any observation point outside a neuron can be calculated by:

$$B = \mu_0 \frac{p \times r}{4\pi r^3} \quad (1)$$

where B is the strength of magnetic field, $\mu_0$ is magnetic permeability in the space, r is the distance from the center of the dipole, p is current dipole, x denotes a cross product, and the bold font indicates a vector.

The current dipole p points along the neuron in the direction of the advancing depolarization wave and has magnitude $$p = \pi a^2 \sigma_i \Delta v_i \quad (2)$$

where a is radius of the dendrite, $\sigma_i$ is electrical conductivity of axoplasma, and $\Delta v_i$ is the change of membrane potential.

Because the length of a dendrite is much longer then the radius of the dendrite, the magnetic field generated by a current dipole at any observation point inside a dendrite can be conveniently calculated according to Ampere's circuital law, which states that a line integral of B around a closed path l is equal to the integral of current density j through any surface s enclosed by the path:

$$\oint B \cdot dl = \mu_0 \int\!\!\int j \cdot ds \quad (3)$$

where • denotes a dot product. Considering the cylindrical symmetry of a dendrite and assuming a uniform current density, the magnitude of the field at observation point r is related to the intracellular current, $i_i$, by:

$$B = \mu_0 \frac{r}{2\pi a^2} i_i \quad (4)$$

By combining Equations 1 and 4, the neuronal magnetic fields at any observation point can be calculated.

Figure 9:
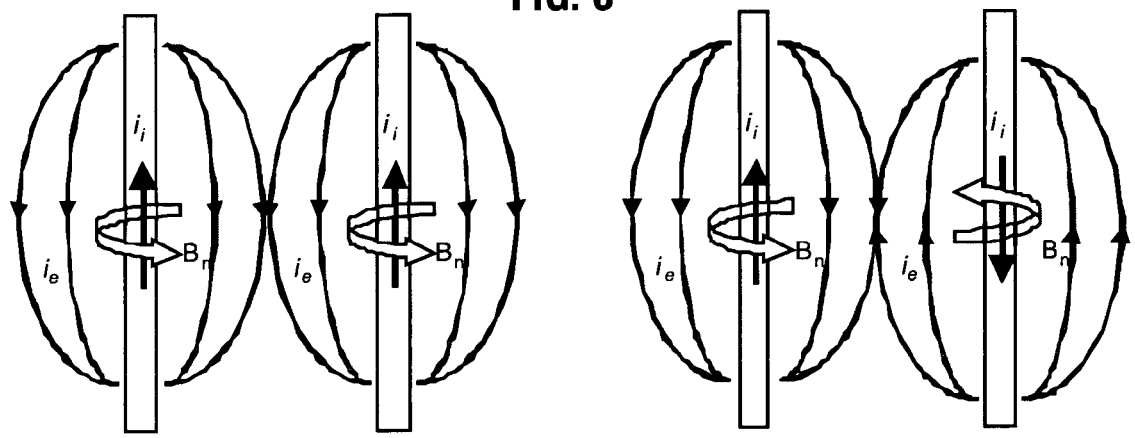
FIG. 9 is a representation of a two dipole system showing parallel (left) and anti-parallel (right) configurations.

In a simple two-dipole system with parallel (two dipoles in the same direction) and anti-parallel (two dipoles in the opposite direction) configurations, the magnetic field at any observation point is a vector summation of the magnetic field generated by each dipole at that point. Such a configuration is shown in FIG. 9. Referring to FIG. 9, shown are configurations of a two-dipole system having parallel (left) and anti-parallel (right) configurations. Parameters used for calculating the magnetic fields are: radius of the dendrites a=0.5 µm, electrical conductivity of axoplasma $\sigma_i$=2 $\Omega^{-1}\text{m}^{-1}$, and membrane potential $\Delta v_i$=75 mV.

As calculated, neuronal magnetic fields increase with distance r; peak on the surface of the dendrites; and then quickly decline. The fields are strongly localized, concentrated in and around the dendrites.

Orientations of neuronal magnetic field, $B_n$, may take any possible direction. The component of $B_n$ parallel to the $B_0$ (of the MRI scanner) will cause the spins at a point (x, y, z) in the transverse plane to acquire additional phases, $\phi_1$(x, y, z), which depend on strengths of the local neuronal magnetic field, $B_n$(x, y, z, t).

$$\begin{aligned}\varphi_1(x, y, z) &= \int_0^{TE} \gamma B_{n\|}(x, y, z, t) dt \\ &= \int_0^{TE} \gamma B_{n\perp}(x, y, z, t) \cos(\theta) dt\end{aligned} \quad (5)$$

where TE represents echo-time, $B_{n//}$(x, y, z, t) is the parallel component of $B_n$(x, y, z, t), θ is angle between $B_0$ and $B_n$, and γ represents gyromagnetic ratio.

The majority of $B_{n\perp}$, which is the component of $B_n$ perpendicular to the $B_0$, will have no net effects on the spins. Only a small fraction of $B_{n\perp}$ at the Larmor frequency will act like a $B_1$ field to rotate the spins at a point (x, y, z) away from the x-y plane. Additional phases, $\phi_2$(x, y, z), generated by the neuronal magnetic field may be approximated by:

$$\varphi_2(x, y, z) = \int_0^{TE} \gamma f B_{n\perp}(x, y, z, t) dt \quad (6)$$
$$= \int_0^{TE} \gamma f B_n(x, y, z, t) \sin(\theta) dt$$

where f is the fraction of $B_{n\perp}$ at the Larmor frequency. The value of f is typically very small. The $\phi_2$, therefore, can be ignored.

Neuronal magnetic fields could be detected, at least in theory, by mapping either phases or magnitudes of MRI signals. The phase shift for a voxel is an integral of $\phi_1$(x, y, z) over the voxel. It is interesting to note that the magnetic fields, $B_n$, in the parallel dipole configuration are 180° out of phase. The average phase shift for an image voxel is then close to zero. Similarly, average phase shift for anti-parallel configuration is also near zero.

Figure 10:
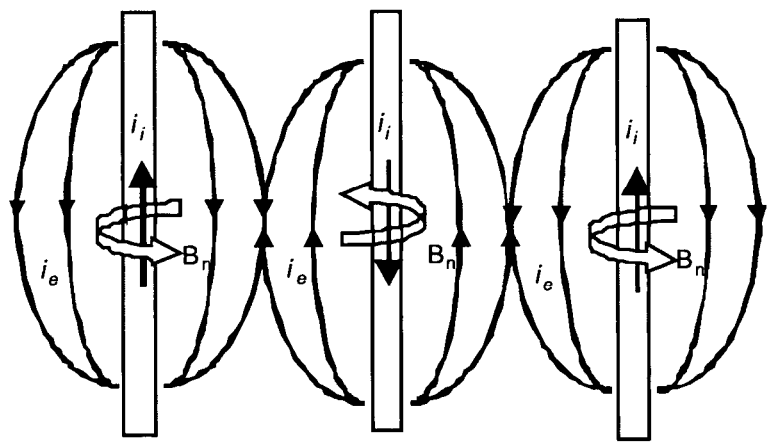
FIG. 10 is a representation of two adjacent two dipole systems in an anti-parallel configuration.

An image voxel typically consists of many neurons. In a two adjacent two-dipole system in anti-parallel configuration, as shown in FIG. 10, magnetic fields in a two-dipole system are always opposite to that in the adjacent two-dipole systems. The integration of $B_n$ (average phase shift) over an image voxel is again approximately zero. While the analysis is based on a simple two-dipole model, the conclusion holds in more complex situations. The direction of magnetic fields on the left side of a current dipole is always opposite to that on the right. Thus, phases of MRI signals will always destructively add. In short, detecting neuronal magnetic fields by mapping MRI phase shifts will not succeed.

Mapping neuronal activity with MRI by detecting magnetic fields induced by neural firing is straightforward. The magnitude of the MRI signal observed at a point (x, y, z) after 90° radio-frequency excitation is related to phase changes induced by the neuronal magnetic field by:

$$s(x,y,z) \propto \rho(x,y,z) \cos(\phi_1(x,y,z)) \quad (7)$$

where $\rho$(x, y, z) is spin density, and $\phi_1$(x, y, z) is defined by equations (5). The MRI signal for an image voxel is an integral of s(x, y, z) over the voxel:

$$S = \int_0^{\Delta x} \int_0^{\Delta y} \int_0^{\Delta z} s(x, y, z) dx\, dy\, dz \quad (8)$$

where $\Delta x$, $\Delta y$, and $\Delta z$ is the dimensions of the voxel. By substituting Equations 5 and 7 to Equation 8, the MRI signal is related to TE by:

$$S \propto \int_0^{\Delta x} \int_0^{\Delta y} \int_0^{\Delta z} \rho(x, y, z) \cos\left(\int_0^{TE} \gamma B_n(x, y, z, t) \cos(\theta) dt\right) dx\, dy\, dz \quad (9)$$

Equation 9 implies that the MRI signal depends on both the strength and orientation of neuronal magnetic fields. When $B_n$ is perpendicular to $B_0$, no MRI change will be induced by neuronal magnetic fields.

Because the component of $B_n$ perpendicular to $B_0$ does not generate significant MRI signal changes, focus may be placed on estimating the effects of the $B_n$ component parallel to the $B_0$ field.

As discussed, an image voxel typically consists of millions of dendrites. Let us first consider that the dendrites are uniformly distributed in a voxel with parallel or anti-parallel configurations and then generalizing the model later.

MRI signal changes can be calculated by substituting the magnetic field distribution to Equation 9. When the dipoles are perpendicular to the $B_0$ field, the relationship between MRI signal changes and the number of dendrites firing simultaneously is plotted in FIG. 11. When the dipoles are parallel to the $B_0$ field, majorities of neuronal magnetic fields are perpendicular to the $B_0$ field. MRI signal changes are very small (near to 0).

Figure 11:
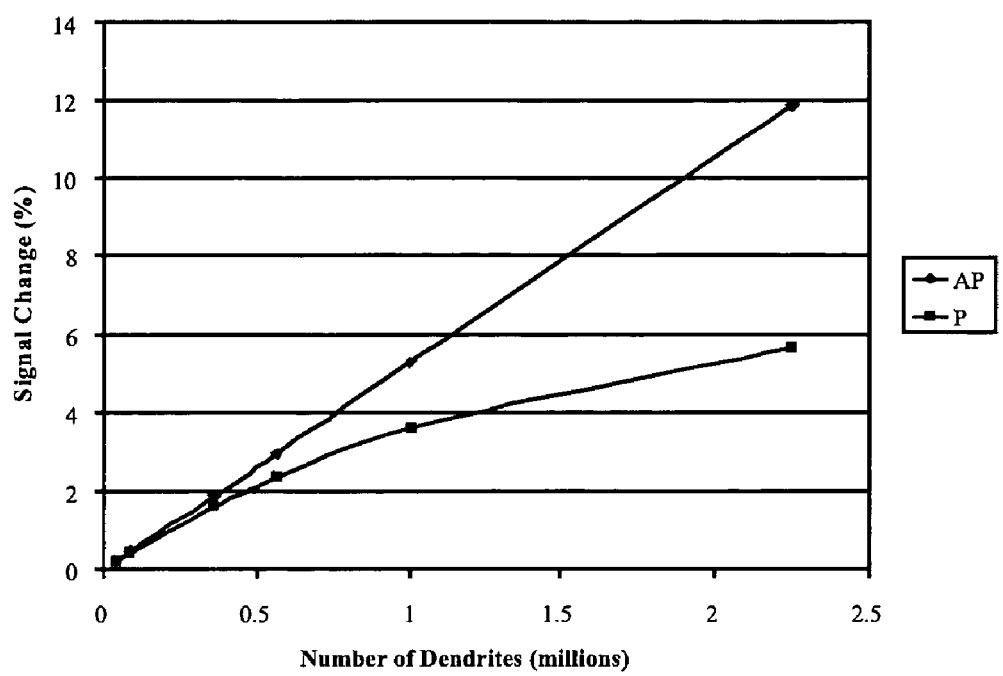
FIG. 11 is a graphical representation of a percentage of signal change versus number of dendrites for parallel and anti-parallel configurations in accordance with one embodiment of the present invention.

The MRI signal change depends on orientations, configurations, and number of dendrites firing simultaneously. As used herein "orientation" means the spatial relationship between neuronal magnetic fields and the $B_0$ field. As used herein, "configuration" is the spatial relationship between dendrites (current dipoles). When angles between dendrites change, it will change magnitudes and orientations of magnetic fields. As shown in FIG. 11, an anti-parallel configuration creates higher signal changes compared to a parallel configuration. The number of dendrites firing simultaneously also plays an important role on the MRI signal changes. However, the exact number of dendrites firing at any given time during echo time TE is unknown and may be estimated. For FIG. 11, the parameters used for calculating the MRI signal changes are: radius of the dendrites a=0.5 μm, electrical conductivity of axoplasma $\sigma_i$=2 $\Omega^{-1}m^{-1}$, TE=100 ms, and membrane potential $\Delta v_i$=75 mV, uniform spin density across the voxel. The number of dendrites here means the average number of dendrites fired during echo time TE for a typical MRI voxel. A conventional estimate is about 100,000 pyramidal cells per square millimeter of cortex, each with tens to thousands of synapses. For a typical MRI voxel of 3×3 mm$^2$, synchronous activation of 0.1% to 1% dendrites could bring up the number of dendrites firing simultaneously to about 0.1 to 1 million. If so, the MRI signal changes should be about 0.44% to 3.6% for parallel configuration and 0.46% to 5.3% for anti-parallel configuration, which should be detectable.

The above analyses are based on the assumption of rather simple configurations of dendrites: parallel or anti-parallel configurations. The real configurations of dendrites in the brain are typically much more complex. If the dipoles of a parallel configuration rotated by an angle α are still perpendicular to the $B_0$ field, MRI signal changes are in the range defined by the parallel (the lower limit) and the anti-parallel configurations (the upper limit) (FIG. 11). However, if the dipoles being rotated are no longer perpendicular to the $B_0$ field, MRI signal changes will decrease. In the worst case where the rotated dipoles are parallel to the $B_0$ field, MRI signal changes will decrease by about 50%.

So far, we have only considered a uniform distribution of dendrites in a voxel. The distributions of dendrites are actually not uniform in the brain. A general approach taken for the non-uniform distribution is sub-dividing a voxel into multiple subvoxels. Dendrite distribution in each subvoxel is approximated by a uniform distribution. The MRI signal change for the voxel can then be computed by calculating the weighted-average (weighted by the sizes of subvoxels) of the signal changes for each subvoxel. Our findings indicate that MRI signal change is dependent on the average dendrite density, but independent of dendrite distributions for the anti-parallel configuration. For parallel configuration, the MRI signal change is insensitive to dendrite distributions for low dendrite densities (<15000 dendrites/mm³) and are slightly smaller than that for uniform distribution when dendrite densities are high (>15000 dendrites/mm³).

Magnetic fields generated by neural firing on the scalp detectable by MEG based on the model may be estimated. The magnetic fields outside the brain are strongly dependent on the configurations of dendrites. An anti-parallel configuration will generate no net magnetic field on the scalp. A parallel configuration will generate a magnetic field of $7\times10^{-12}$ T on the scalp 4 cm away from the current source, assuming no attenuation by the scalp and one million dendrites firing simultaneously. The orientations of dendrites in the brain are very complex and are neither simply parallel nor simply anti-parallel. The magnetic fields on the scalp should then be somewhere between that generated by an anti-parallel configuration and that generated by a parallel configuration, i.e., between 0 to $7\times10^{-12}$ T. MEG detection is also dependent on the orientation of neuronal magnetic fields relative to the MEG detector. When the neuronal magnetic field is parallel to the detecting coil, no signal will be detected. The actual magnetic field reported by a MEG experiment is about $10^{-13}$ T and is in the range estimated based on our model.

For BOLD contrast or other magnetic field inhomogeneity, the effects on MRI signals are typically modeled by a $T_2^*$ effect. The relative signal change created by a BOLD contrast is described by:

$$\Delta S = \frac{S_1 - S_0}{S_0} \approx R_2' TE \quad (10)$$

where $S_0$ and $S_1$ are MRI signals without and with BOLD effect, and $R'_2$ is the external decay rate due to the BOLD contribution. The $R'_2$ is independent to TE.

Figure 12:
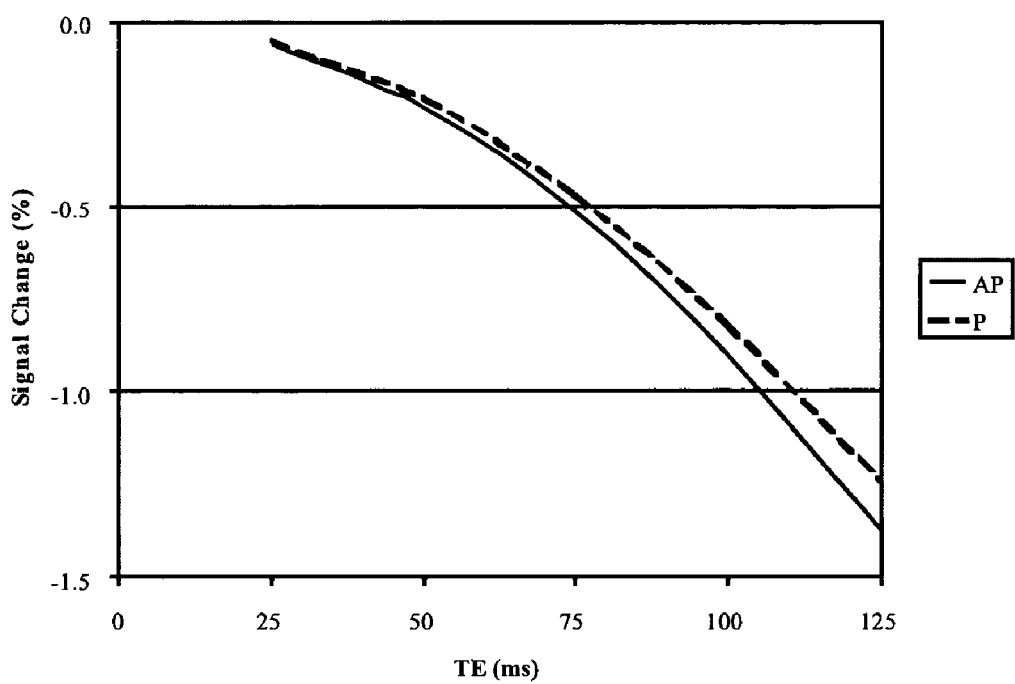
FIG. 12 is a graphical representation of computed MRI signal changes with echo time for parallel and anti-parallel configurations in accordance with an embodiment of the present invention.

The TE dependence of MRI signal changes due to neuronal magnetic fields can be computed based on Equation 9. The relationship of TE and MRI signal changes is given by Equation 11 and is plotted in FIG. 12, which shows computed MRI signal changes with TE for parallel (P) and anti-parallel (AP) configurations. It is very interesting to see a nonlinear relationship between TE and MRI signal changes. When TE doubled, the MRI signal changes increase by an average 3.8 times. The unusually strong dependence of MRI signal changes on the echo-time TE provides an excellent opportunity to experimentally validate the model.

$$\Delta S = \frac{S - S_0}{S_0} \quad (11)$$

$$= \frac{\int_0^{\Delta x}\int_0^{\Delta y}\int_0^{\Delta z} \rho(x,y,z)\cos\left[\int_0^{TE} \gamma B_n(x,y,z,t)\cos(\theta)dt\right]dxdydz}{\int_0^{\Delta x}\int_0^{\Delta y}\int_0^{\Delta z} \rho(x,y,z)dxdydz} - 1$$

To verify the TE depedence, experiments were performed on three subjects for three different TEs. The signal changes for all activated brain areas were measured. The experimental data show a nonlinear relationship between TE and MRI signal changes (FIG. 8) and are supportive to the theoretical modelling.

These results demonstrate that MRI signal changes induced by neuronal magnetic fields are in detectable levels. A MRI magnitude map may provide a better result than a phase map. Amplitudes of msMRI signals depend on orientations, configurations, and density of dendrites. Furthermore, the MRI signal changes have a nonlinear relationship with TE. The strong dependence of MRI signal changes on TE have been confirmed by experimental results.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method for measuring neural activity comprising:
directly detecting, using magnetic resonance imaging, regional neural activity in response to stimulating a subject with a hemodynamically neutral stimulation to induce a hemodynamically neutral state in the subject undergoing magnetic resonance imaging from and concurrently with transient magnetic fields induced by the regional neural activity, the direct detecting without measurement of hemodynamic or metabolic changes as a result of the regional neural activity and occurring in a time window prior to hemodynamic activity in the subject as a result of the regional neural activity; and
spatially and temporally localizing the regional neural activity using at least a portion of the detected transient magnetic fields.

2. The method of claim 1, wherein the magnetic resonance imaging comprises applying an asymmetric pulse sequence to the subject.

3. The method of claim 2, wherein the asymmetric pulse sequence comprises a gradient-echo echo-planar image pulse sequence.

4. The method of claim 3, wherein the asymmetric pulse sequence comprises a repetition time of between approximately 40 and 10,000 milliseconds, an echo time of between approximately 10 and 200 milliseconds, and a flip angle of between approximately 10 and 180 degrees.

5. The method of claim 1, wherein the direct detecting comprises measuring magnetic resonance imaging signal magnitude changes.

6. The method of claim 1, wherein the hemodynaically neutral stimulation comprises providing rapid stimuli to the subject.

7. The method of claim 1, further comprising performing a second nervous system measurement technique to conjoin with the magnetic resonance imaging.

8. The method of claim 7, wherein the second nervous system measurement technique measures at least one of cerebral hemodynamic, metabolic, and neural activity.

9. The method of claim 1, further comprising detecting intrinsic rhythms of a nervous system of the subject using the regional neural activity.

10. The method of claim 1, further comprising diagnosing a disorder of a nervous system of the subject using the regional neural activity.

11. The method of claim 1, further comprising analyzing a drug effect on a nervous system of the subject using the regional neural activity.

12. The method of claim 1, further comprising detecting the regional neural activity in a predetermined window after the hemodynamic activity.

13. A method comprising:
stimulating a subject with a hemodynamically neutral stimulation;

performing magnetic resonance imaging on the subject; and directly mapping electromagnetic activity of the subject via the magnetic resonance imaging from electromagnetic activity without a temporal delay, wherein the direct mapping is to directly detect regional neural activity of the subject responsive to the stimulating from and concurrently with electromagnetic activity induced by regional neural activity, without measurement of hemodynamic or metabolic changes as a result of the regional neural activity.

14. The method of claim 13, wherein the magnetic resonance imaging comprises applying an asymmetric pulse sequence to the subject.

15. The method of claim 14, wherein the asymmetric pulse sequence comprises a gradient-echo echo-planar image pulse sequence.

16. The method of claim 13, further comprising measuring magnetic resonance imaging signal magnitude changes.

17. The method of claim 13, further comprising performing a second nervous system measurement technique to conjoin with the magnetic resonance imaging.

18. The method of claim 13, further comprising detecting intrinsic rhythms of a nervous system of the subject via the electromagnetic activity.

19. The method of claim 13, further comprising diagnosing a disorder of a nervous system of the subject based on the electromagnetic activity.

20. The method of claim 13, further comprising directly mapping the electromagnetic activity based on magnetic resonance imaging data obtained in a predetermined time window prior to or after the hemodynamic changes.

21. An article comprising a computer readable medium containing instructions that if executed, enable a system to:
   directly detect, using magnetic resonance imaging, regional neural activity in response to a hemodynamically neutral stimulus in a subject undergoing magnetic resonance imaging from and concurrently with transient magnetic fields induced by the regional neural activity and without inferring the regional neural activity from hemodynamic or metabolic changes, in a time window prior to hemodynamic activity as a result of the regional neural activity; and
   spatially and temporally localize the regional neural activity using at least a portion of the detected transient magnetic fields.

22. The article of claim 21, further comprising instructions that if executed enable the system to measure magnetic resonance imaging signal magnitude changes.

23. A system for measuring neural activity comprising:
   a magnetic resonance imaging scanner having a plurality of magnets to generate a magnetic field around a subject,
   a stimulus generator to provide a hemodynamically neutral stimulus to the subject; and
   a controller coupled to the magnetic resonance imaging scanner and including a storage to store instructions that enable the controller to obtain data to directly detect a magnitude of magnetic resonance signals representing a neuronal magnetic field induced by neuronal activity in response to a hemodynamically neutral stimulus without measurement of hemodynamic or metabolic changes as a result of the regional neural activity, wherein the controller is to obtain the data in a first time window prior to hemodynamic activity in the subject as a result of the regional neural activity, a second time window after the hemodynamic activity, or a third time window in which a hemodynamic response to the hemodynamically neutral stimulus is at a steady state, wherein the controller is to cause the magnetic resonance imaging to use an asymmetric pulse sequence.

24. The system of claim 23, wherein the plurality of magnets comprises a main magnet and a gradient magnet.

25. The system of claim 23, wherein the controller is further adapted to directly map electromagnetic activity of the subject via the magnitude of the magnetic resonance signals.

26. The system of claim 25, wherein the map comprises a spatial and temporal localization of the neuronal activity of the subject.

27. The system of claim 23, further comprising a second controller coupled to the magnetic resonance imaging scanner to provide an asymmetric pulse sequence to the magnetic resonance imaging scanner.

28. The system of claim 23, further comprising a measurement device to measure a response of the subject to the specific stimulus.

29. An article comprising a computer readable medium containing instructions that if executed, enable a system to:
   receive magnitude resonance signals from a subject of a magnetic resonance imaging system prior to or after hemodynamic changes of the subject as a result of neuronal activity of the subject responsive to a hemodynamically neutral stimulus; and
   process the magnitude resonance signals to measure the neuronal activity from and concurrently with neural electromagnetic changes of the subject instead of from the hemodynamic changes or metabolic changes induced by the neural electromagnetic changes.

30. The article of claim 29, further comprising instructions that if executed enable the system to localize the neuronal activity spatially and temporally.

31. The article of claim 29, further comprising instructions that if executed enable the system to generate an image based on the neuronal activity.

* * * * *